United States Patent
Carlson et al.

(10) Patent No.: US 11,739,352 B1
(45) Date of Patent: Aug. 29, 2023

(54) METHODS OF SUBJECTING BIOMASS SOLIDS TO AT LEAST ONE DISRUPTION PROCESS AFTER THE BIOMASS SOLIDS HAVE BEEN EXPOSED TO AT LEAST FERMENTATION, AND RELATED SYSTEMS

(71) Applicant: POET Research, Inc., Sioux Falls, SD (US)

(72) Inventors: David Charles Carlson, Brandon, SD (US); Brady Christopher Clavel, Yankton, SD (US); Katherine Lois Kokes, Tabor, SD (US); David D. Bushong, Sioux Falls, SD (US); Blake A. Schnell, Harrisburg, SD (US)

(73) Assignee: POET Research, Inc., Sioux Falls, SD (US)

( * ) Notice: Subject to any disclaimer, the term of this patent is extended or adjusted under 35 U.S.C. 154(b) by 0 days.

(21) Appl. No.: 17/115,747

(22) Filed: Dec. 8, 2020

Related U.S. Application Data

(60) Provisional application No. 62/945,264, filed on Dec. 9, 2019.

(51) Int. Cl.
  *C12P 7/10* (2006.01)
  *C12P 7/14* (2006.01)
  *C08H 8/00* (2010.01)
  *C12P 19/14* (2006.01)

(52) U.S. Cl.
  CPC ............... *C12P 7/10* (2013.01); *C08H 8/00* (2013.01); *C12P 19/14* (2013.01); *C12P 2201/00* (2013.01)

(58) Field of Classification Search
  None
  See application file for complete search history.

(56) References Cited

U.S. PATENT DOCUMENTS

| | | | |
|---|---|---|---|
| 4,448,881 A * | 5/1984 | Muller | C12F 3/10 435/162 |
| 6,648,500 B2 | 11/2003 | Fedorov et al. | |
| 6,726,133 B2 | 4/2004 | Hahn et al. | |
| 7,101,691 B2 | 9/2006 | Kinley et al. | |
| 7,842,484 B2 | 11/2010 | Lewis | |
| 7,919,289 B2 | 4/2011 | Lewis | |
| 7,919,291 B2 | 4/2011 | Lewis et al. | |
| 8,008,516 B2 | 8/2011 | Cantrell et al. | |
| 8,409,639 B2 | 4/2013 | Lewis et al. | |

(Continued)

FOREIGN PATENT DOCUMENTS

WO 2014201439 A1 12/2014

OTHER PUBLICATIONS

International Preliminary Report on Patentability for International Application No. PCT/US2014/042432, dated Dec. 15, 2015, (6 pages).

(Continued)

*Primary Examiner* — Richard C Ekstrom
(74) *Attorney, Agent, or Firm* — Kagan Binder, PLLC

(57) ABSTRACT

The present disclosure relates to methods and systems of fermenting that include, after the fermentable composition has been exposed to fermentations conditions to produce biochemical, exposing at least a portion of a fermentable composition to a disruption process to disrupt at least a portion of insoluble solid component. After the fermentable composition has been exposed to a disruption process, the fermentable composition can be exposed to fermentation conditions again to product biochemical.

24 Claims, 9 Drawing Sheets

(56) References Cited

U.S. PATENT DOCUMENTS

| | | |
|---|---|---|
| 8,409,640 B2 | 4/2013 | Lewis et al. |
| 8,497,082 B2 | 7/2013 | Lewis |
| 8,597,919 B2 | 12/2013 | Lewis |
| 8,702,819 B2 | 4/2014 | Bootsma |
| 8,748,141 B2 | 6/2014 | Lewis et al. |
| 9,012,191 B2 | 4/2015 | Lee |
| 9,018,404 B2 | 4/2015 | Brophy |
| 9,061,987 B2 | 6/2015 | Bootsma |
| 9,394,505 B2 | 7/2016 | Sticklen et al. |
| 9,695,449 B2 | 7/2017 | Bootsma |
| 10,113,007 B2 | 10/2018 | Kohl |
| 10,584,304 B2 | 3/2020 | Schnell et al. |
| 2008/0277264 A1 | 11/2008 | Sprague |
| 2012/0028325 A1 | 2/2012 | Herring et al. |
| 2012/0244590 A1 | 9/2012 | Lee |
| 2013/0121891 A1 | 5/2013 | Dieker et al. |
| 2014/0127772 A1* | 5/2014 | Kohl .............. C08B 30/042 435/165 |
| 2014/0283226 A1 | 9/2014 | Lewis et al. |
| 2016/0168596 A1 | 6/2016 | Lynd et al. |
| 2018/0235167 A1 | 8/2018 | Lewis et al. |
| 2019/0119711 A1 | 4/2019 | Lee |
| 2019/0376002 A1 | 12/2019 | Urban et al. |
| 2020/0165540 A1 | 5/2020 | Schnell et al. |

OTHER PUBLICATIONS

International Search Report for International Application No. PCT/US2014/042432, dated Nov. 4, 2014, (2 pages).

Balch et al., "Lignocellulose fermentation and residual solids characterization for senescent switchgrass fermentation by Clostridium thermocellum in the presence and absence of continuous in situ ball-milling†", Energy & Environmental Science, vol. 10, pp. 1252-1261, 2017, (11 pages).

Detroy et al., "Biomass Conversion: Fermentation Chemicals and Fuels", CRC Critical Reviews in Microbiology, vol. 10, Issue 3, pp. 203-228, 1983, (26 pages).

Ghosh et al., "Rheological properties of corn stover slurries during fermentation by Clostridium thermocellum", Biotechnology for Biofuels, vol. 11, pp. 1-12, 2018, (12 pages).

Archambault-Leger et al., "Integrated analysis of hydrothermal flow through pretreatment", Biotechnology for Biofuels, vol. 5, pp. 1-10, 2012, (10 pages).

Mais et al., "Enhancing the Enzymatic Hydrolysis of Cellulosic Materials Using Simultaneous Ball Milling", Applied Biochemistry and Biotechnology, vol. 98, No. 100, pp. 815-832, 2002, (19 pages).

Shimoda et al., "Ethanol Conversion of Spent Mushroom Culture Medium by the Ball-Vibration Simultaneous Saccharification and Fermentation System", Mokuzai Gakkaishi, vol. 54, No. 6, pp. 340-345, 2008, (6 pages).

Watanabe et al., "Analysis of Fermentation Inhibiting during Ball-Vibration Simultaneous Saccharification and Fermentation Used for Ethanol Production from Spent Mushroom Culture Medium", Mokuzai Gakkaishi, vol. 55, No. 6, pp. 363-368, 2009, (6 pages).

Shimoda et al., "Conversion of waste mushroom bed to ethanol," Journal of the Wood Society, vol. 54, No. 6, p. 340-345 (2008), (6 pages), (Full English, Machine Translation from Google Translate).

* cited by examiner

METHODS OF SUBJECTING BIOMASS SOLIDS TO AT LEAST ONE DISRUPTION PROCESS AFTER THE BIOMASS SOLIDS HAVE BEEN EXPOSED TO AT LEAST FERMENTATION, AND RELATED SYSTEMS

RELATED APPLICATIONS

The present nonprovisional patent application claims the benefit of commonly owned provisional Application having ser. no. 62/945,264, filed on Dec. 9, 2019, wherein the entirety of said provisional application is incorporated herein by reference.

BACKGROUND

The present disclosure relates to methods and systems of using biomass as a renewable feedstock in a biorefinery to form monosaccharide, which can be converted by microorganisms into biochemical.

There is a continuing need for improved systems and methods of fermenting biomass with microorganisms to convert monosaccharide into biochemical.

SUMMARY

The present disclosure includes embodiments of a method of fermenting, wherein the method includes:
a) providing a fermentable composition, wherein the fermentable composition includes:
  i) biomass, wherein the biomass includes a solid component and a saccharide component; and
  ii) a microorganism that can convert monosaccharide into a biochemical,
b) exposing the fermentable composition to conditions to convert at least a first portion of the saccharide component into a biochemical via fermentation;
c) after performing step (b) for at least 12 hours,
  i) exposing at least a portion of the fermentable composition to a disruption process to disrupt at least a portion of insoluble solid component; and
  ii) during and/or after (c)(i), converting at least a second portion of the saccharide component into biochemical via fermentation.

The present disclosure also includes embodiments of a method of fermenting, wherein the method includes:
a) providing a fermentable composition, wherein the fermentable composition includes:
  i) biomass, wherein the biomass includes a solid component and a saccharide component; and
  ii) yeast,
b) exposing the fermentable composition to conditions to convert at least a first portion of the saccharide component into alcohol via fermentation;
c) after forming an alcohol titer in step (b) of at least 1% v/v based on the fermentable composition,
  i) exposing at least a portion of the fermentable composition to a disruption process to disrupt at least a portion of insoluble solid component; and
  ii) during and/or after (c)(i), converting at least a second portion of the saccharide component into alcohol via fermentation.

The present disclosure also includes embodiments of a method of fermenting, wherein the method includes:
a) providing a fermentable composition, wherein the fermentable composition includes:
  i) biomass, wherein the biomass includes a solid component and a saccharide component; and
  ii) yeast;
b) exposing the fermentable composition to conditions to convert at least a first portion of the saccharide component into alcohol via fermentation, and reproduce yeast;
c) after the yeast is at a density of at least $1 \times 10^6$ yeast cells per milliliter of fermentable composition in step (b),
  i) exposing at least a portion of the fermentable composition to a disruption process to disrupt at least a portion of insoluble solid component; and
  ii) during and/or after (c)(i), converting at least a second portion of the saccharide component into alcohol via fermentation.

The present disclosure also includes embodiments of a method of fermenting, wherein the method includes:
a) hydrolyzing polysaccharide and/or oligosaccharide present in biomass into monosaccharide to form a fermentable composition, wherein the fermentable composition includes the monosaccharide, a microorganism that can convert monosaccharide into a biochemical and a water component;
b) after step (a), exposing the fermentable composition to conditions to convert at least a first portion of the saccharide component into biochemical via fermentation;
c) during at least a portion of step (b),
  i) exposing at least a portion of the fermentable composition to a disruption process to disrupt at least a portion of insoluble solid component; and
  ii) during and/or after (c)(i), converting at least a second portion of the saccharide component into biochemical via fermentation.

DETAILED DESCRIPTION

Figure 1:
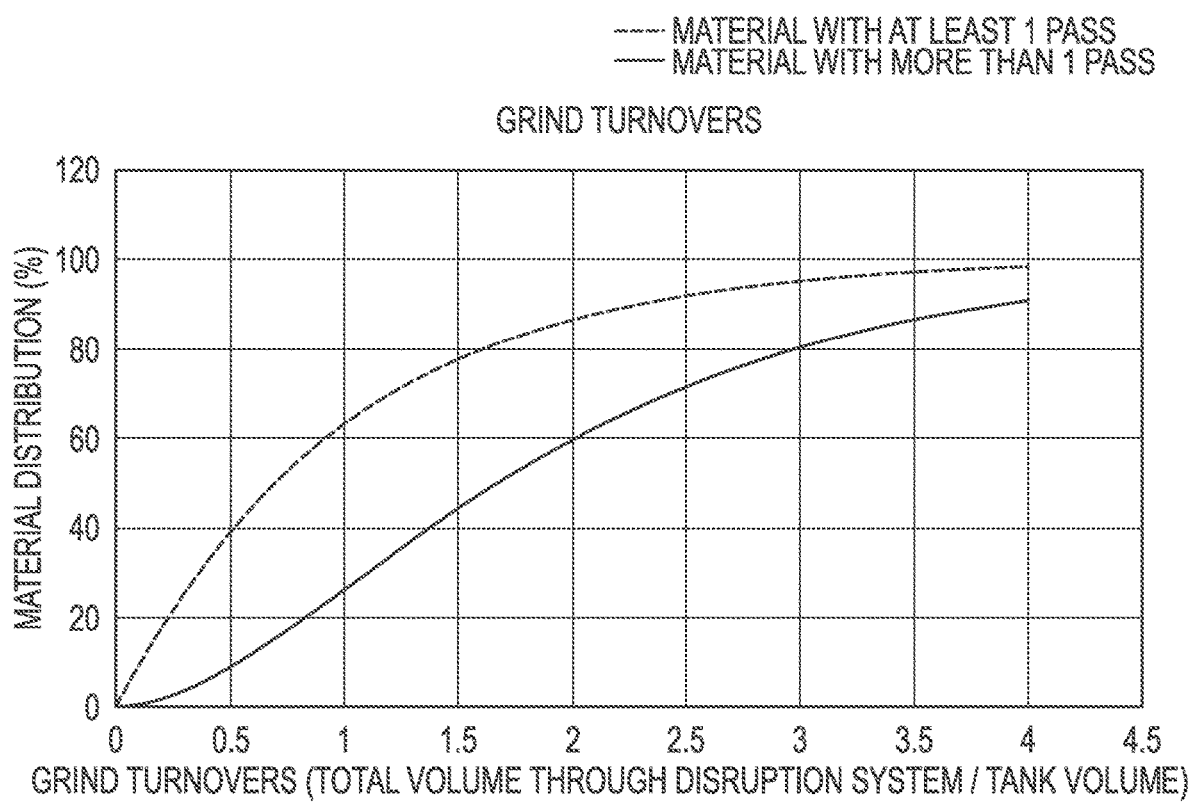
FIG. 1 is a graph showing the relationship between grind turnovers (total volume through the disruption system/total fermentation system volume that disruption system recycles back to) and what percentage of the material in the fermentation system has been through the disruption system one or more times.

The present disclosure involves disrupting of at least a portion of an insoluble solid component of biomass after the solid component has been exposed to a fermentation process for a period of time. Non-limiting examples of a fermentation process include fermentation that occurs sequentially after a polysaccharide hydrolysis process (e.g., jet-cooking and/or enzymatic hydrolysis), or simultaneous saccharification and fermentation ("SSF"). While not being bound by theory, it is believed that disrupting a biomass insoluble solid component after the insoluble solid component has been exposed to a fermentation process (e.g., simultaneous saccharification and fermentation) allows the insoluble solid component to first be at least partially degraded due to enzymatic hydrolysis and conversion of sugars to biochemical, thereby facilitating further breakdown by physical disruption. The further breakdown of the biomass by physical disruption can improve the accessibility of at least a portion of remaining saccharide component to enzymes and/or microorganisms and the formation of biochemical and/or recovery of co-products from beer before biochemical recovery (e.g. distillation) and/or from whole stillage after biochemical recovery.

Providing a fermentable composition

According to the present disclosure, a disruption process is applied to at least a portion of a fermentable composition. As used herein, a "fermentable composition" includes biomass having at least a saccharide component, and microorganisms that can convert at least a first portion of monosaccharide present in the saccharide component into a biochemical via fermentation. A fermentable composition may have undergone or is undergoing at least some fermentation, but a fermentable composition according to the present disclosure also refers to a composition that can still include insoluble polysaccharide that can be hydrolyzed into monosaccharide, and active microorganisms that can convert monosaccharide that is present in the fermentable composition into biochemical. A fermentable composition has a liquid component and a solid component. The liquid component includes at least water. The liquid component can also include oil (e.g., corn oil) that is bound up in the structure of the biomass and insoluble in water. The solid component includes at least a portion of the biomass, which includes one or more soluble solids and one or more insoluble solids. For example, solid component can include polysaccharide (e.g., fiber (e.g., cellulose and/or hemicellulose), starch, and the like), and/or lignin as insoluble solids. The solid component can also include one or more soluble solids such as monosaccharides and oligosaccharides. In some embodiments, as described below, an entire fermentable composition (the entire liquid and solid components) can be exposed to a disruption process according to the present disclosure. In some embodiments, as also described below, a fermentable composition can be separated into a liquid fraction and a solid fraction followed by exposing the liquid fraction and/or the solid fraction to a disruption process according to the present disclosure. As used herein, a "solid fraction" and a "liquid fraction" can each have a liquid component and a solid component. The solid fraction has a higher concentration of solid component as compared to the liquid fraction and the fermentable composition prior to being separated. Also, each of the liquid fraction and the solid fraction can include polysaccharide (e.g., starch), oligosaccharide, and monosaccharide (e.g., glucose).

As used herein, a "saccharide component" can include one or more of polysaccharide, oligosaccharide, and monosaccharide. In some embodiments, the saccharide component includes at least one or more monosaccharides that can be converted into a biochemical by a microorganism, one or more oligosaccharides and one or more polysaccharides. A wide variety of biomass can be used according to the present disclosure such as sugar beets, sugar cane, grains, legumes, crop residues (e.g., corn stover), grasses, and woody plants. Non-limiting examples include corn, sorghum, wheat, rice, barley, soybean, rapeseed, oats, millet, rye, corn stover, straw, bagasse and the like. In some embodiments, biomass can include whole ground grain formed via a dry-grind process.

Optionally, a fermentable composition can include one or more additional ingredients such as nutrients and/or other ingredients to facilitate fermentation. Such ingredients can be exogenously combined with the biomass and/or may be endogenous to the biomass.

Figure 2:
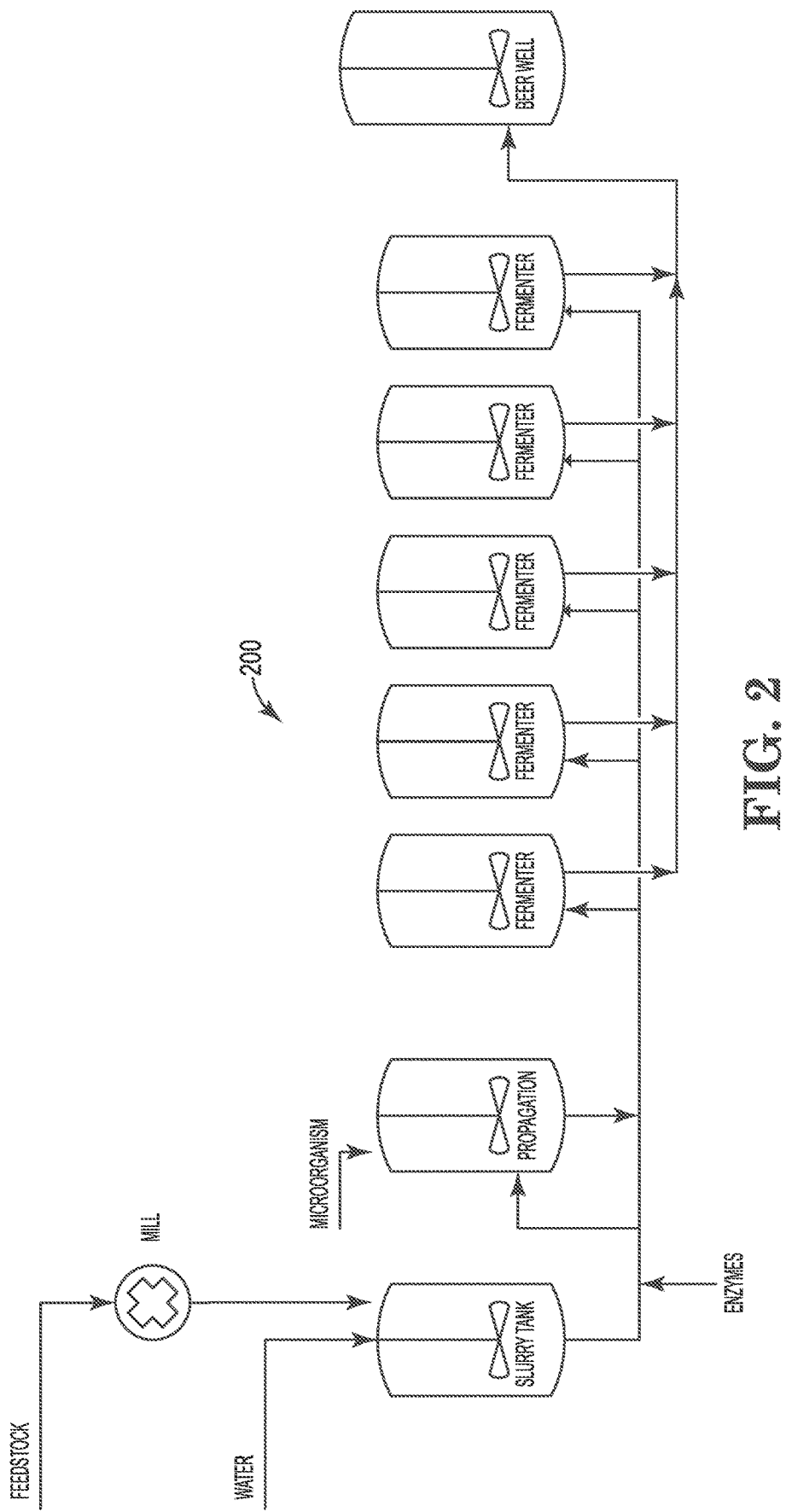
FIG. 2 shows a fermentation process flow diagram in which grain is milled, slurried with water, enzymatically hydrolyzed at low temperature utilizing raw starch enzymes to saccharify the starch.
Figure 3:
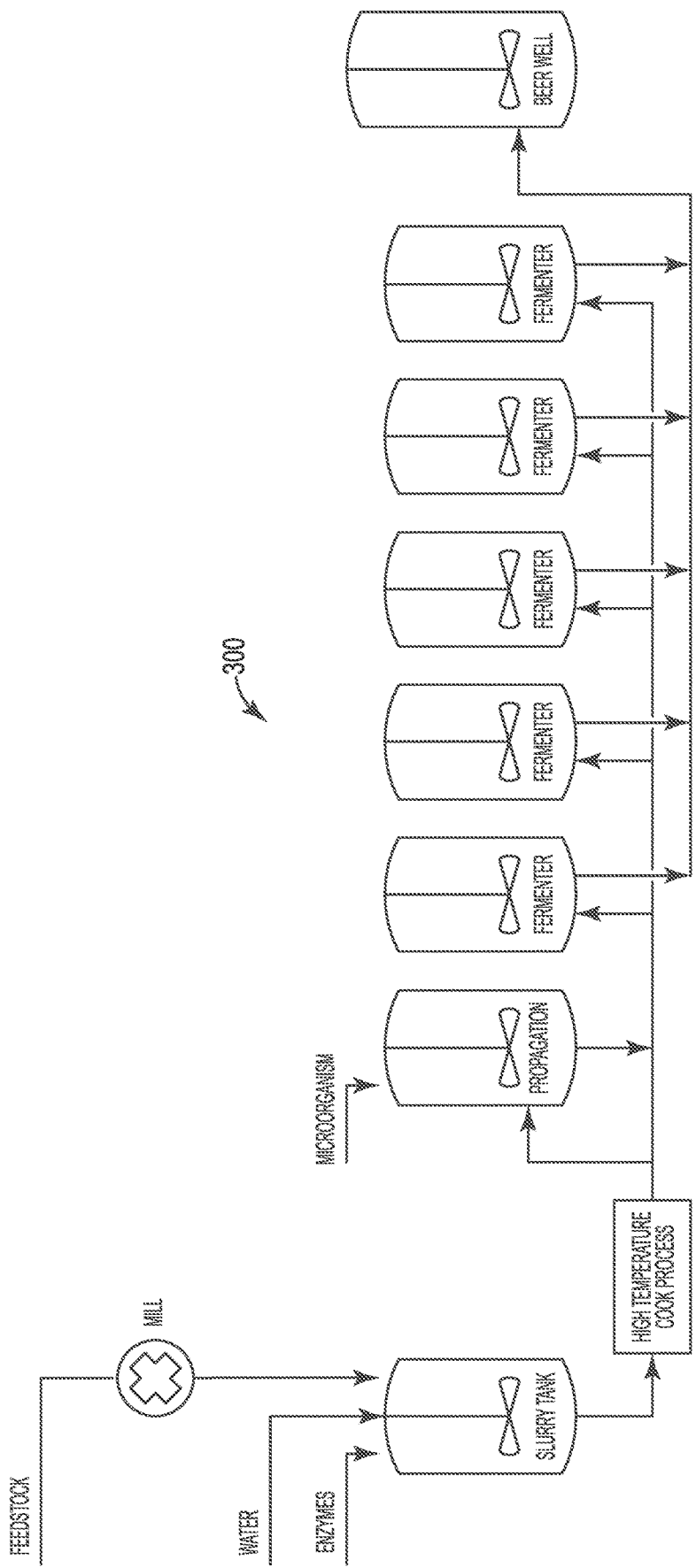
FIG. 3 shows a fermentation process flow diagram in which grain is milled, slurried with water, cooked to gelatinize the starch, enzymatically hydrolyzed to liquefy the starch, and enzymatically hydrolyzed to saccharify the starch.
Figure 4:
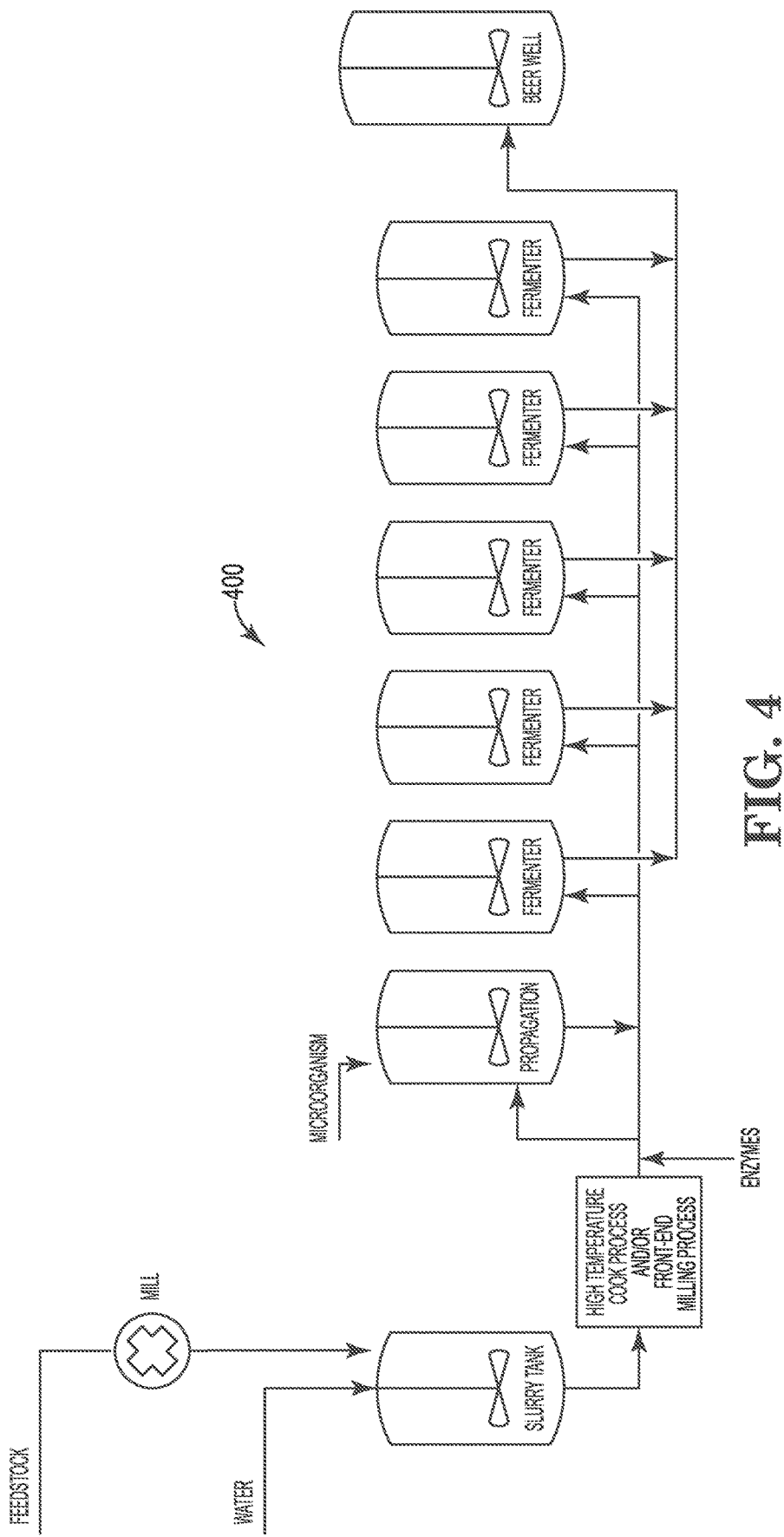
FIG. 4 shows a fermentation process flow diagram in which milled grain is formed into a slurry and the slurry is milled prior to being exposed to fermentation conditions.

Disrupting biomass solids after the biomass solids have been exposed to fermentation for a period of time may be used in a variety of monosaccharide conversion processes. FIGS. 2-4 depict non-limiting, illustrative examples of monosaccharide conversion processes to which the present disclosure relates.

FIG. 2 illustrates a grain-to-ethanol process 200 in which grain is milled, slurried with water, enzymatically hydrolyzed at low temperature utilizing raw starch enzymes to saccharify the starch, and fermented. In some embodiments, saccharification and fermentation are performed simultaneously as shown in FIG. 2. In some embodiments, a relatively low temperature saccharification process (whether used in SSF or separate saccharification and fermentation) involves enzymatically hydrolyzing at least a portion of the starch in the aqueous slurry at a temperature below starch gelatinization temperatures, so that saccharification occurs directly from the raw native insoluble starch to soluble glucose while bypassing conventional starch gelatinization conditions. Starch gelatinization temperatures are typically in a range of 57° C. to 93° C. depending on the starch source and polysaccharide type. Converting raw starch to glucose is described in U.S. Pat. Nos. 7,842,484 (Lewis), 7,919,289 (Lewis), 7,919,291 (Lewis et al.), 8,409,639 (Lewis et al.), 8,409,640 (Lewis et al.), 8,497,082 (Lewis), 8,597,919 (Lewis), 8,748,141 (Lewis et al.), 2014-0283226 (Lewis et al.), and 2018-0235167 (Lewis et al.), wherein the entirety of each patent document is incorporated herein by reference. In one embodiment, saccharification includes using one or more enzymes (e.g., with alpha-amylases and gluco-amylases) to enzymatically hydrolyze at least a portion of the starch in the aqueous slurry at a temperature below 40° C. or less to produce a slurry that includes glucose. In some embodiments, enzymatic hydrolysis occurs at a temperature in the range of from 25° C. to 35° C. to produce a slurry that includes glucose.

FIG. 3 illustrates another grain-to-ethanol process 300 in which grain is milled, slurried with water, cooked to gelatinize the starch, enzymatically hydrolyzed to liquefy the starch, enzymatically hydrolyzed to saccharify the starch, and fermented.

FIG. 4 illustrates another grain-to-ethanol process 400 in which milling of the slurry occurs before any fermentation occurs.

Each of FIGS. 5-8 (discussed below) depicts a non-limiting example of a system according to the present disclosure that can disrupt biomass solids after the biomass solids have been exposed to fermentation conditions.

Figure 5:
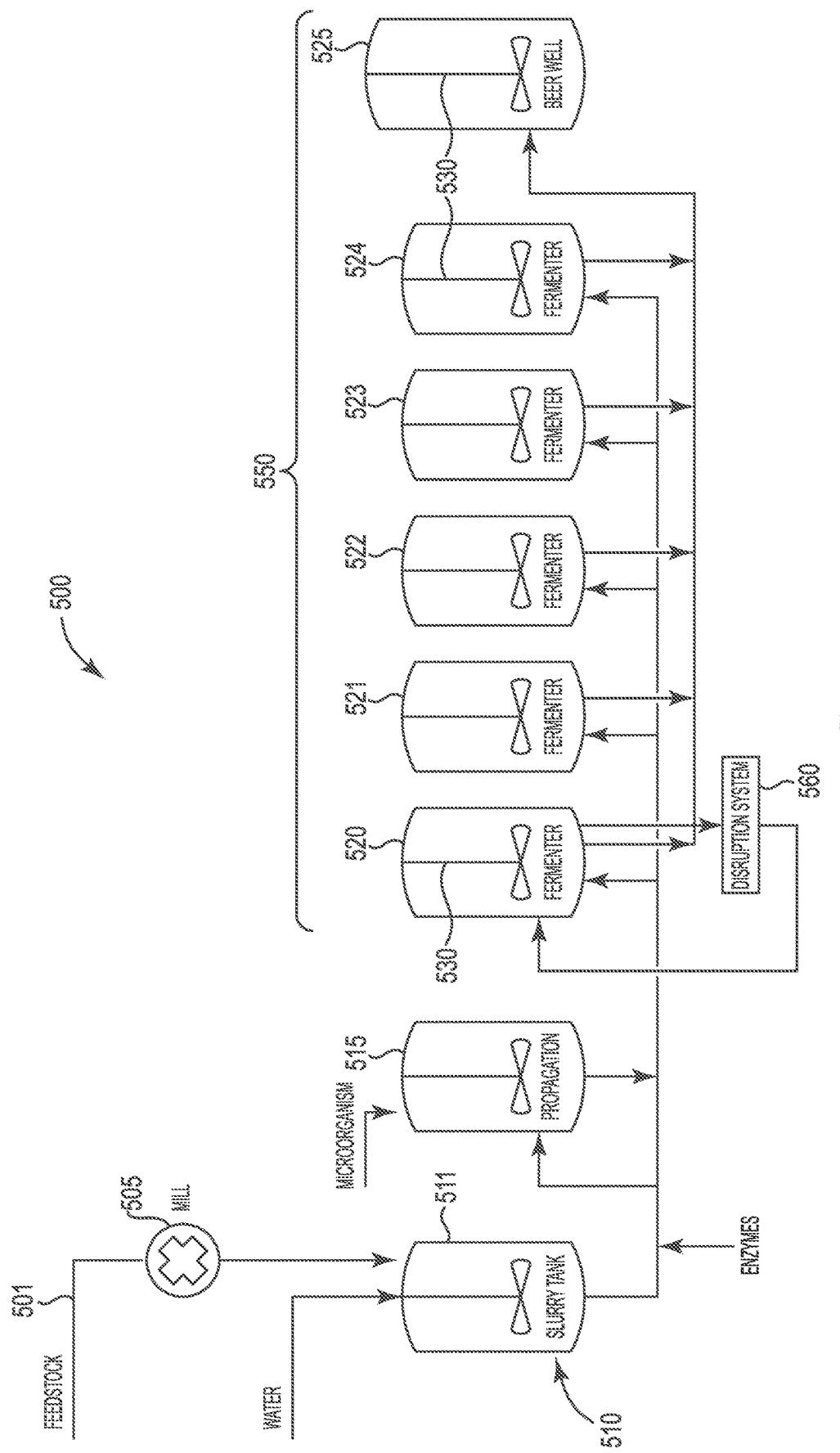
FIG. 5 shows a fermentation process flow diagram of an embodiment according to the present disclosure.

For illustration purposes, FIG. 5 shows a non-limiting embodiment of the present disclosure and is described in the context of a process 500 of forming ethanol from corn grain.

With respect to forming a fermentable composition using corn grain, process 500 includes providing grain feedstock (corn kernels) 501 that is ground into small particles. As shown in FIG. 5 for illustration purposes, in some embodiments corn grain can be prepared via dry milling (e.g., hammer milling) 505 to produce whole ground corn having a medium-to-fine grind. In some embodiments, corn grain can be dry-fractionated to separate components of the corn grain (e.g., germ) from each other and then recombined in a desired ratio for further processing.

In some embodiments, the corn grain can be ground so that a substantial portion, e.g., a majority, of the ground corn grain fits through a sieve with a 0.1-5.0 mm screen, or even a 0.1-0.5 mm screen. For example, in an embodiment, about 70% or more, of the ground corn can fit through a sieve with a 0.1-0.5 mm screen. As shown in FIG. 5, ground corn can be mixed with an appropriate amount of water in a slurry tank 510 to form an aqueous composition (e.g., a slurry) 511 that includes one or more enzymes that can hydrolyze a polysaccharide and/or an oligosaccharide into monosaccharide for fermentation of the resulting monosaccharides. In an embodiment, whole ground corn can be mixed with liquid at about 20 to about 50 wt-% or about 25 to about 45 wt-% dry whole ground corn based on the total weight of the slurry. The whole ground corn can include starch, fiber, protein, oil, endogenous enzymes, amino acids, etc.

In some embodiments, additional grinding of biomass into smaller particles prior to fermentation may improve ethanol yield, however grinding prior to fermentation can be energy intensive, especially if the particles have not been exposed very long or at all to other process conditions that can help break the insoluble solid particles down into particles that grind relatively easier. Methods for grinding biomass, e.g. corn, into finer particles prior to fermentation include dry methods such as passing ground corn through one or more additional hammer mills, ball mills and/or roller mills or wet methods such as passing a ground corn slurry through one or more additional mills such as a disc mill, roller mill, colloid mill, ball mill or other type of milling device.

As mentioned above, fermentation according to the present disclosure can be performed according to a variety of protocols. For example, fermentation can occur sequentially after a polysaccharide hydrolysis/saccharification process (e.g., jet-cooking and/or enzymatic hydrolysis). Sequential hydrolysis and fermentation can also be referred to as separate hydrolysis and fermentation (SHF). As another example, saccharification and fermentation can occur simultaneously according to what is known as "simultaneous saccharification and fermentation" ("SSF").

An example of disrupting biomass solids after at least a portion of fermentation has begun will be illustrated in the context of SSF.

Simultaneous Saccharification and Fermentation

In the illustrative raw starch hydrolyzing example of FIG. 5, a fermentable composition can be exposed to conditions so that a microorganism can convert at least a first portion of the saccharide component into a biochemical via fermentation. Exemplary microorganisms include ethanologens, butanologens, and the like. Exemplary microorganisms include yeast and bacteria. For example, yeast may be used to convert the sugars to ethanol. Suitable yeast includes any variety of commercially available yeast, such as commercial strains of Saccharomyces cerevisiae. In some embodiments, fermenting can include conditions suitable for growth of the microorganism as well as production of a biochemical.

As shown in FIG. 5, the slurry ("grain mash composition") can be combined with a microorganism such as yeast from a source such as a yeast propagation system 515 to form a fermentable composition that is transferred to fermentation system 550 where at least a portion of starch in the fermentable composition is hydrolyzed by the enzymes present to produce monosaccharides which are simultaneously metabolized by a microorganism into a target biochemical product. For example, sugar (glucose, xylose, mannose, arabinose, etc.) that is generated from saccharification can be fermented into one or more biochemicals (e.g., butanol, ethanol, and the like). Systems for producing more than one biochemical from the sugar can be integrated together or be separate.

A fermentation system according to the present disclosure can include one or more vessels that can expose a fermentable composition to conditions suitable for converting a saccharide such as glucose to a biochemical such as ethanol. As used herein, a "vessel" refers to any vessel that permits a biochemical to be formed from a microorganism via fermentation. In some embodiments, a vessel can refer to a bioreactor adapted or configured to expose a fermentable composition to one or more desirable conditions such as pH, temperature, aeration, stirring and the like. Non-limiting examples of vessels that can expose a fermentable composition to conditions suitable for converting a saccharide such as glucose to a biochemical such as ethanol include fermenters, beer wells, and the like.

A fermenter can be operated according to a variety of protocols such as batch fermentation or continuous fermentation (continuous feed and discharge from a vessel such as a fermenter).

While not being bound by theory, it is believed that exposing a fermentable composition to fermentation conditions for a period of time can cause insoluble solid component (insoluble non-saccharide and/or insoluble saccharide solid) present in the fermentable composition to be at least partially degraded, which weakens its structure and makes it more susceptible to further breakdown by physical disruption. Providing physical disruption after the fermentable composition has been exposed to fermentation conditions for a period of time can accelerate the breakdown and conversion of remaining saccharide component, which can result in a more complete conversion of monosaccharide into biochemical. While not being bound by theory, it is believed that the improved breakdown of the solid component of the biomass improves the accessibility of the saccharide component to enzymes and/or microorganisms and the formation of biochemical and/or recovery of co-products from beer before distillation and/or from whole stillage after distillation. Also, while not being bound by theory, it is believed that one or more processes that may occur during fermentation conditions (e.g., enzymatic hydrolysis, soaking, swelling, and/or the like) can cause insoluble solid component (insoluble non-saccharide and/or insoluble saccharide solid) present in the fermentable composition to be at least partially degraded, which weakens its structure and makes it more susceptible to further breakdown by physical disruption.

As shown in FIG. 5, fermentation system 550 includes five fermenters 520, 521, 522, 523, and 524, and one beer well 525. A fermentable composition is formed by combining the streams from slurry tank 510 and yeast propagation system 515. Fermentable composition can be transferred to fill each of said fermenters 520, 521, 522, 523, and 524 to a desired level so that they can operate in a batch manner. When fermentation is complete, the fermented mash (beer) is transferred to beer well 525 and another fermentation batch can be initiated in the fermenter that was emptied into beer well 525. In some embodiments, a beer well can function as a "buffer" in system 500 to manage throughput and facilitate the transition from batch fermentation to downstream processes, especially continuous downstream processes such as distillation, oil extraction, etc.

As shown in FIG. 5, each of the five fermenters 520, 521, 522, 523, and 524, and beer well 525 have a stirring mechanism 530 that can be operated to keep the contents therein well mixed. Non-limiting examples of stirring mechanisms 530 include a top entry agitator, recirculation pump, gas-pulsing system, aeration, large bubble mixing (pulsair), side entry agitator, combinations thereof, and the like.

Sequential Saccharification and Fermentation (also referred to as Separate Hydrolysis and Fermentation (SHF))

Alternatively, a biomass conversion process may include a dedicated saccharification process that is separate from a fermentation process (either in the same or separate vessel). For example, after forming an aqueous slurry that includes the biomass, e.g. corn material from milling system 505, or other feedstocks, as described above, the aqueous slurry can be subjected to saccharification in one or more slurry tanks to break down (hydrolyze) at least a portion of the polysaccharides, e.g. starch, cellulose, hemicellulose, etc., into monosaccharides, e.g. glucose, xylose, mannose, arabinose, etc., that can be used by microorganisms (e.g., yeast) in a subsequent fermentation system. Multiple slurry tanks, if used, can be arranged in series and/or parallel.

Saccharification can be performed by a variety of techniques. For example, heat and/or one or more enzymes can be used to form one or more monosaccharides by saccharifying one or more oligosaccharides and/or one or more polysaccharides that are present in the ground corn.

Disruption

According to the present disclosure, at least a portion of the fermentable composition that includes insoluble solid component of biomass is exposed to a disruption process. A disruption process according to the present disclosure disrupts at least a portion of insoluble solid component of biomass after the insoluble solid component has been exposed to fermentation conditions for a period of time. While not being bound by theory, disrupting the insoluble solid component after the insoluble solid component has been exposed to fermentation can improve the physical breakdown and/or accessibility of saccharide component (soluble and/or insoluble) to enzymes and/or microorganisms, thereby improving the formation of biochemical (e.g., alcohol) and/or recovery of co-products (e.g., grain oil and the like) from beer mash before distillation and/or from whole stillage after distillation. A disruption process according to the present disclosure imparts energy to insoluble solid component to disrupt it and expose or release insoluble saccharide component (e.g., starch) and/or oil. For example, a disruption process can break down and/or physically manipulate fiber and/or lignin to expose insoluble saccharide to enzyme that can hydrolyze polysaccharide into oligosaccharide and/or monosaccharide. As another example, a disruption process can physically break down and/or physically manipulate recalcitrant, insoluble solid polysaccharide so that it can be accessed by enzyme for hydrolysis. A disruption process according to the present disclosure is different from mixers such as mixer 530, which have the primary purpose of mixing the contents of the vessel to promote uniform mixtures even though some incidental physical breakdown of solid components may occur due to such mixing. It is noted that in some embodiments a disruption process can be described as a relatively much higher intensity mixing operation (unlike mixer 530) that can "free up" components such as enzyme, saccharide and the like that were previously unavailable for conversion to biochemical and/or recovery.

One or more of a wide variety of disruption processes can be used to disrupt solid component of a biomass according to the present disclosure. Non-limiting examples of disruption processes include milling systems and methods, cavitation systems and methods, ultrasonic systems and methods, emulsion technology systems and methods, rotary pulsation systems and methods, sonication systems and methods, magnetostriction systems and methods, ferromagnetic materials systems and methods, combinations of these, and the like. Two or more such disruption systems can be used in a disruption process according to the present disclosure, and can be the same type or different type. Two or more disruption systems can be arranged in a wide variety of configurations including coupled together in series and/or parallel.

In some embodiments, a disruption process can include electrical to mechanical, mechanical to electrical, pulse, and sound based vibrations at varying speeds. This can provide varying frequencies over a wide range of frequencies, which can be effective for disrupting the solid component of biomass.

The flowrate through a given "disruption" apparatus of a disruption process according to the present disclosure can depend on a variety of factors such as how much solid and liquid is present in the feed stream, the type of biomass, the scale of operation, and the like. In some embodiments, the flowrate of a feed stream into a disruption apparatus can be from 5 to 200 gallons per minute, from 20 to 100 gallons per minute, or even from 30 to 90 gallons per minute.

In some embodiments, a disruption process can include subjecting solid component of biomass to mechanical milling such as with one or more disc mills, roller mills, a colloid mills, disk refiners, homogenizers, rotary impact mills (beater mills), jet mills, tumbling mills (e.g., ball mills, tube mills, pebble mills, rod mills, and the like), impact mills, cone mills, centrifugal mills, high sheer pumps, high sheer rotor stator mixers, screw presses, French presses, and combinations thereof.

While not being bound by theory, it is believed that certain sonic methods create low pressure around a solid particle of biomass and induce cavitation that leads to disruption of the particle structure. The disrupted particle can increase access of enzymes to polysaccharide and/or oligosaccharide.

In some embodiments, a disrupting process includes vibrating solid component of biomass and cavitating fluid containing the solid component. This can result in disrupting the solid component and/or decreasing the size of the solid component. In some embodiments, a disruption process includes treating the solid component of biomass with emulsion technology, with rotary pulsation, with magnetostriction, and/or with ferromagnetic materials. This can result in disrupting the solid component and/or decreasing the size of the solid component. In some embodiments, a disruption process includes sonicating the solid component. This can result in disrupting the solid component and/or decreasing the size of the solid component.

In some embodiments, a disruption process can include employing sound waves (e.g., for reducing the size of biomass solid component). The sound waves can be ultrasound. A disruption process can include sonicating the solid component at a frequency (e.g., measured in kHz), power (e.g., measured in watts), and for a time effective to reduce (or to assist in reducing) the particle size of the solid component. For example, a disruption process can include sonicating the solid component at 20,000 Hz and up to about 3000 W for a sufficient time and at a suitable temperature. Such sonicating can be carried out with a commercially available apparatus, such as high powered ultrasonics available from ETREMA (Ames, Iowa).

In some embodiments, a disruption process can include employing rotary pulsation (e.g., for reducing the size of biomass solid component). For example, a disruption process can include rotary pulsating the solid component at a frequency (e.g., measured in Hz), power (e.g., measured in watts), and for a time effective to reduce (or to assist in reducing) the particle size of the solid component. Such rotary pulsating can be carried out with known apparatus, such as apparatus described in U.S. Pat. No. 6,648,500, the disclosure of which is incorporated herein by reference.

In some embodiments, a disruption process can include employing pulse wave technology (e.g., for reducing the size of particles of the solid component of biomass). For example, a disruption process can include rotary pulsing biomass solid component at a frequency (e.g., measured in Hz), power (e.g., measured in watts), and for a time effective to reduce (or to assist in reducing) the particle size of the solid component. Such pulsing can be carried out with known apparatus, such as apparatus described in U.S. Pat. No. 6,726,133, the disclosure of which is incorporated herein by reference.

Examples of disruption processes that can be used in the present disclosure are also described in U.S. Pat. No. 8,748,141 (Lewis et al.), wherein the entirety of said patent is incorporated herein by reference.

As mentioned, allowing at least a portion of fermentation to have been performed on the fermentable composition can help "soften" or "break down" at least a portion of the solid component and facilitate breaking the solid component down even further using a disruption process as described herein.

A disruption process can be initiated after fermentation has begun based on a variety of parameters. Non-limiting examples of parameters include time of fermentation, concentration of biochemical (e.g., alcohol titer), and/or microorganism density. In some embodiments, a disruption process can be performed on a fermentable composition at a point in the overall process at which the microorganisms used to form biochemical (e.g., yeast) are present in quantities sufficient to withstand disruption operations according to the present disclosure. Also, fermentation conditions may be at a point where the desired microorganism (e.g., yeast) can outcompete undesirable microorganisms (e.g., lactic acid bacteria) due to one or more of population size of the microorganism, alcohol level, and the like. For example, at the beginning of a yeast fermentation, there tends to be plenty of "food" available for yeast and undesirable bacteria to grow and less alcohol to inhibit growth of undesirable bacteria. Waiting for fermentation to proceed for a time period can allow yeast to be at much better competitive advantage over undesirable bacteria when conditions such as disruption processes according to the present disclosure begin that can be disruptive to both yeast and undesirable bacteria.

In some embodiments, at least a portion of fermentable composition can be exposed to a disruption process after exposing the fermentable composition to conditions to convert at least a first portion of the saccharide component into a biochemical via fermentation for a time period of at least 12 hours, at least 20 hours, or even at least 24 hours (e.g., from 12 to 100 hours, from 15 to 80 hours, or even from 20 to 75 hours). In some embodiments, at least a portion of the fermentable composition can be exposed to a disruption process after being exposed to fermentation conditions for 10 hours (e.g., after 10-20 hours, after 12-20 hours, or even after 15-20 hours). In some embodiments, a fermentable composition is exposed to fermentation conditions when it is introduced into a fermenter (e.g., time equals zero when filling a fermenter begins). In some embodiments, the time period can be measured after filling a fermenter 70 to 100 percent full with a fermentable composition at a rate from 10 gpm to 2000 gm, from 20 gpm to 1500 gpm, or even from 50 gpm to 1500 gpm, where the fermenter has a capacity of at least 10,000 gallons, at least 15,000 gallons, or even at least 20,000 gallons, e.g., from 10,000 to 1,000,000 gallons.

In some embodiments, at least a portion of fermentable composition including the fermenting microorganism (e.g. yeast) can be exposed to a disruption process after the fermentable composition has an alcohol titer (concentration) of at least 1% v/v based on the fermentable composition (e.g., from 1 to 25% v/v based on the fermentable composition, from 5 to 25% v/v based on the fermentable composition, from 10 to 25% v/v based on the fermentable composition, or even from 10 to 15% v/v based on the fermentable composition). Exposing a fermentable composition to a disruption process according to the present disclosure after a sufficient concentration of alcohol is present can protect the fermentation composition from being contaminated or infected if the fermentable composition is discharged from the fermenter to a disruption system that is external to the fermenter. In some embodiments, a sufficient concentration of alcohol that can protect the fermentation composition from being contaminated or infected is greater than 12% v/v based on the fermentable composition, greater than 12.5% v/v based on the fermentable composition, greater than 13% v/v based on the fermentable composition, or even greater than 14% v/v based on the fermentable composition.

In some embodiments, at least a portion of fermentable composition including yeast can be exposed to a disruption process after the yeast is present in the fermentable composition at a concentration of at least $1 \times 10^6$ yeast cells per milliliter of fermentable composition. In some embodiments, at least a portion of fermentable composition including yeast can be exposed to the disruption process after the yeast is present at a density from $1 \times 10^6$ to $15 \times 10^8$ yeast cells per milliliter of fermentable composition, from $3 \times 10^6$ to $10 \times 10^8$ yeast cells per milliliter of fermentable composition, or even from $3 \times 10^6$ to $8 \times 10^8$ yeast cells per milliliter of fermentable composition.

A fermentable composition can be processed through a disruption process in a continuous or intermittent manner. In some embodiments, a disruption process can be performed continuously for a desired time period that correlates to one or more target parameters (e.g., residual starch, particle size, ethanol titer, oil recovery yield, and combinations thereof). For example, a disruption process can be performed for a time period from 10 to 100 hours, from 15 to 60 hours, or even from 15 to 40 hours. In some embodiments, one or more parameters can be monitored and used as feedback to control a disruption process according to the present disclosure. For example, one or more of residual starch, particle size, ethanol titer, oil recovery yield, and combinations thereof can be monitored and compared against target values to determine if a disruption process should be adjusted. For example, it can be determined that one or more of disruption process intensity (e.g., rpm of a milling process), time interval of an intermittent process, and the like may be adjusted to achieve a target value of a monitored parameter.

According to the present disclosure, the fermentable composition can be subjected to a disruption process as-is (e.g., as a slurry) or, optionally, as mentioned above, a fermentable composition can be separated into a liquid fraction and a solid fraction using one or more solid-liquid separation apparatuses followed by exposing the liquid fraction and/or the solid fraction to a disruption process according to the present disclosure. In some embodiments, separating the fermentable composition prior to a disruption process such as milling permits the solid component to be at least partially dewatered, which can be advantageous because, for example, the liquid flowrate through the milling equipment can be reduced, thereby reducing the overall power requirement and/or increasing the milling efficiency by increasing the viscosity of the feed stream to the milling equipment to help prevent solid component from "slipping" past mechanical milling components.

Non-limiting examples of a solid-liquid separation apparatus that can separate a fermentable composition include a centrifuge (e.g., a decanting centrifuge, a disk-stack centrifuge (e.g., a two-phase or three-phase disk stack centrifuge), a gravity screen, a hydroclone, a filter press, a rotary paddle screen, a screw press, a gravity settler (settling tank), a membrane filter, a cartridge filter, and combinations thereof. Multiple solid-liquid separation apparatuses can be arranged in any desired manner with respect to each other such as in series and/or parallel relationship.

Referring again to FIG. 5, an embodiment of the present disclosure is illustrated where a disruption system 560 is used to process a fermentable composition after fermenting for a time period as described herein above. As shown in FIG. 5, fermentable composition contained in at least one of fermenters 520, 521, 522, 523, and 524 is exposed to conditions to convert at least a portion of saccharide component into alcohol via fermentation. The disruption system 560 can be integrated into the fermentation system 550 in a variety of ways. For example, a single disruption system 560 may be connected to (e.g., in parallel with) and in fluid communication with each of the fermenters so that the fermentable composition contained in each fermenter 520, 521, 522, 523, and 524 is circulated through the disruption system 560 after exposing the fermentable composition to fermentation conditions for a time period as described herein above. For illustration purposes, FIG. 5 only shows fermenter 520 coupled to disruption system 560. However, one or more valves (not shown) can be adjusted to permit fermentable composition to flow from another fermenter (e.g., 521, 522, 523, or 524) to disruption system 560.

At the desired time, at least a portion of the fermentable composition is exposed to the disruption system 560 to reduce a size of at least a portion of a solid component of the fermentable composition. For example, as shown in the exemplary embodiment of FIG. 5, the fermentable composition is discharged from fermenter 520, passed through the disruption system 560 and at least a portion of the fermentable composition is recycled to a fermenter. For illustration purposes, the "disrupted", fermentable composition is recycled back to the fermenter from which it came (fermenter 520). Alternatively, the disrupted, fermentable composition could be recycled to a different vessel or to multiple vessels (e.g., fermenters).

After being recycled, the disrupted fermentable composition can then be exposed to fermentation conditions to continue fermentation and convert saccharide component into alcohol. The saccharide component in the disrupted fermentable composition can include, e.g., monosaccharide that was present in the fermentable composition prior to being exposed to disruption system 560 as well as additional monosaccharide formed from oligosaccharide and/or polysaccharide as a result of solid saccharide (e.g., starch granules) being disrupted by disruption system 560 and ultimately converted to glucose via one or more enzymes present in the fermentable composition.

The control of flow of fermentable composition from at least one of the fermenters 520, 521, 522, 523, and 524 to the disruption system 560 can be performed using a wide variety of valves and related controls (not shown).

The disruption system 560 configuration shown in FIG. 5 is a recycling disruption system in which a given fermenter 520, 521, 522, 523, and 524 recirculates fermentable composition through the disruption system 560 for a portion of the overall fermentation time of each fermenter 520, 521, 522, 523, and 524 instead of emptying the entire contents of a given fermenter through the disruption system 560 in a "single" pass. Data was generated for such a recycling disruption system that receives and recycles fermentable composition to understand the efficiency of recycling as compared to a single pass system. The data was generated using four fermenters having a total fermentation time of 80 hours in each fermenter, and the contents of each of the fermenters was recirculated through a recycling disruption system (DS) after a time period of between 20 and 40 hours of fermentation. The data was calculated based on a numerical simulation technique assuming a perfectly mixed tank. For illustration purposes, the disruption system for this data was a milling system. As illustrated in Table 1 below, in a recycling disruption scenario, a relatively high portion of the starch granules may pass through the disruption system multiple times in order to permit a desirable percentage of all starch granules making at least one pass through the recycling disruption system. This is also shown graphically in FIG. 1.

TABLE 1

Relationship between number of material passes through a recirculation disruption system and total grind turnovers

| Grind Turnovers (total volume through DS/ fermenter volume) | Material with at least one pass through the DS (%) | Material with more than one pass through the DS (%) |
|---|---|---|
| 1 | 63.4 | 26.4 |
| 2 | 86.6 | 59.5 |
| 3 | 95.1 | 80.2 |
| 4 | 98.2 | 91.0 |

In some embodiments, a fermentable composition can be discharged from a fermenter and through a disruption system (without first being separated into a liquid fraction and solid fraction) and recycled back to the fermenter for a period of time. The total volume of fermentable composition from the fermenter (or fermentations system) passed through the disruption system and recycled back to the fermenter (or fermentation system) divided by the fermenter volume of the fermenter (or fermentation system) that the fermentable composition is recycled back to can be referred to as "grind turnover." In embodiments, the grind turnover may be 10 or less, 6 or less, 5 or less, 4 or less, or even 3 or less. Such recycling through a disruption system for a given number of grind turnovers can be performed for one or more distinct time periods for a given fermentation batch in a fermenter (e.g., once or intermittently for multiple time periods). For example, a fermentable composition can be discharged from a fermenter and through a disruption system and recycled back to the fermenter for a time period ("disruption cycle"), e.g. for a given number of grind turnovers. The recycling can be stopped for a period of time while additional fermentation occurs. After a desired time period has passed, the fermentable composition can again be discharged from the fermenter and through the disruption system and recycled back to the fermenter for another time period, e.g. a given number of grind turnovers, (which may be the same or different from the previous time or set of grind turnovers). In some embodiments, the time-period between successive disruption cycles can be 15 minutes or greater, 30 minutes or greater, 45 minutes or greater, or even 60 minutes or greater. In some embodiments, the time-period between successive disruption cycles can be 15 minutes to 30 hours, from 30 minutes to 25 hours, or even from 1 hour to 20 hours.

In some embodiments, the disruption efficiency in a recycling disruption system scenario as illustrated in FIG. 5 may be improved by at least partially dewatering or concentrating the feed to the disruption system 560 in order to reduce the amount of water being processed through the mill. This may be accomplished by the use of any number of dewatering technologies or concentrating technologies discussed above on the feed stream such as a gravity screen, pressure screen, paddle screen, decanter, hydroclone, evaporator or other suitable type of dewatering equipment or solids concentrating equipment. The use of any type of dewatering equipment can produce a stream concentrated in biomass solid component (solid fraction) that can be fed to the disruption process 560 and a stream with reduced solids (liquid fraction) content can be recycled back to the fermenter. In some embodiments, the liquid fraction includes a large portion of active microorganism (e.g., yeast) that was present in the feed stream. Another approach to dewatering includes a passive dewatering approach, which can involve reducing the mixing power input to a stirring mechanism 530 of each fermenter by either slowing down the mixer or operating the mixer intermittently. This would allow solid component of the fermentable composition (e.g., starch granules) to settle to the bottom of a fermenter. The feed stream to the disruption system could be taken from near the bottom of the fermenter to produce a stream of concentrated solids for the disruption system 560.

In some embodiments, a fermentable composition can be discharged from a fermenter and separated into a liquid fraction and solid fraction, where the solid fraction is passed through a disruption system and recycled back to the fermenter for a period of time such that the total volume of solid fraction through the disruption system divided by the fermenter volume is 5 or less, 4 or less, 3 or less, or even 2 or less. Such recycling through a disruption system for a given number of grind turnovers can be performed for one or more distinct time periods for a given fermentation batch in a fermenter (e.g., once or intermittently for multiple time periods). For example, a solids fraction from a fermenter can be transferred through a disruption system and recycled back to the fermenter for a given number of grind turnovers and then when a desired time period has passed after recycling and additional fermentation has occurred, solids fraction from a fermenter can be transferred through the disruption system and recycled back to the fermenter for another given number of grind turnovers (which may be the same or different from the previous set of grind turnovers). In some embodiments, the time-period between successive sets of grind turnovers can be 15 minutes or greater, 30 minutes or greater, 45 minutes or greater, or even 60 minutes or greater.

In some embodiments, the time-period between successive sets of grind turnovers can be 15 minutes to 30 hours, from 30 minutes to 25 hours, or even from 1 hour to 20 hours.

Optionally, if desired, equipment could be coupled to the discharge of disruption system 560 that separates solid particles based on size and recycles at least a portion of the fermentable composition discharged from disruption system 560 that includes solid particles larger than a target size back through disruption system 560 directly and/or upstream of system 560 such as via slurry tank 510.

Continuing to ferment after fermentable composition has been exposed to disruption process After a fermentable composition has been exposed to a disruption process as described herein, saccharide component present in the fermentable composition can be converted into biochemical via fermentation by the microorganism that was previously present during the initial fermentation period before disruption began. Polysaccharide and oligosaccharide can be hydrolyzed to monosaccharide, which can be converted to biochemical. Advantageously, if desired, additional exogenous microorganism does not need to be added to the fermentable composition after disruption. However, if desired, additional exogenous microorganism can be added to the fermentable composition after disruption. In some embodiments, if a fermentable composition is separated prior to a disruption process into a liquid fraction and solid fraction as discussed above, at least a portion of the microorganism may be transferred from the fermentable composition into the liquid fraction and avoid the disruption process if desired. The liquid fraction including the microorganism can be recycled and/or transferred downstreamto one or more vessels (e.g., fermenters, beer wells, and the like). Also, in some embodiments, at least a portion of the microorganism may have been present in the feed stream that was exposed to a disruption process. For example, microorganism may have been present in the feed stream that was exposed to a disruption process due to being present in a solid fraction that was separated from the fermentable composition prior to a disruption process or microorganism may have been present in a fermentable composition that was transferred from a fermenter to a disruption process without first being separated into a liquid fraction and solid fraction.

At least a portion of the saccharide component that is present in the fermentable composition after being exposed to a disruption process can be made available for fermentation due to the disruption process. By integrating a disruption process and fermentation together at least a portion of solid polysaccharide such as corn starch granules will already be partially degraded by the enzymes prior to the disruption.

In addition, in some embodiments, subjecting partially degraded starch granules to disruption system 560 may reduce the particle size of the granules to a target particle size using less overall energy as compared to if the original starch granules had been reduced to the same target size due to grinding prior to fermentation (e.g., by the "front end milling process" shown in FIG. 4 and/or mill 505). For example, in some embodiments the energy input of initial dry milling system 505 for milling corn can be reduced so the milled particle size after milling system 505 is larger than a target particle size. The disruption system 560 can then reduce the particle size to the target particle size, but at an energy input such that the total energy input for a given target particle size is less for the sum of mill 505 and disruption system 560, as compared to if dry mill 505 is used to reduce granules to the same target particle size.

Figure 6:
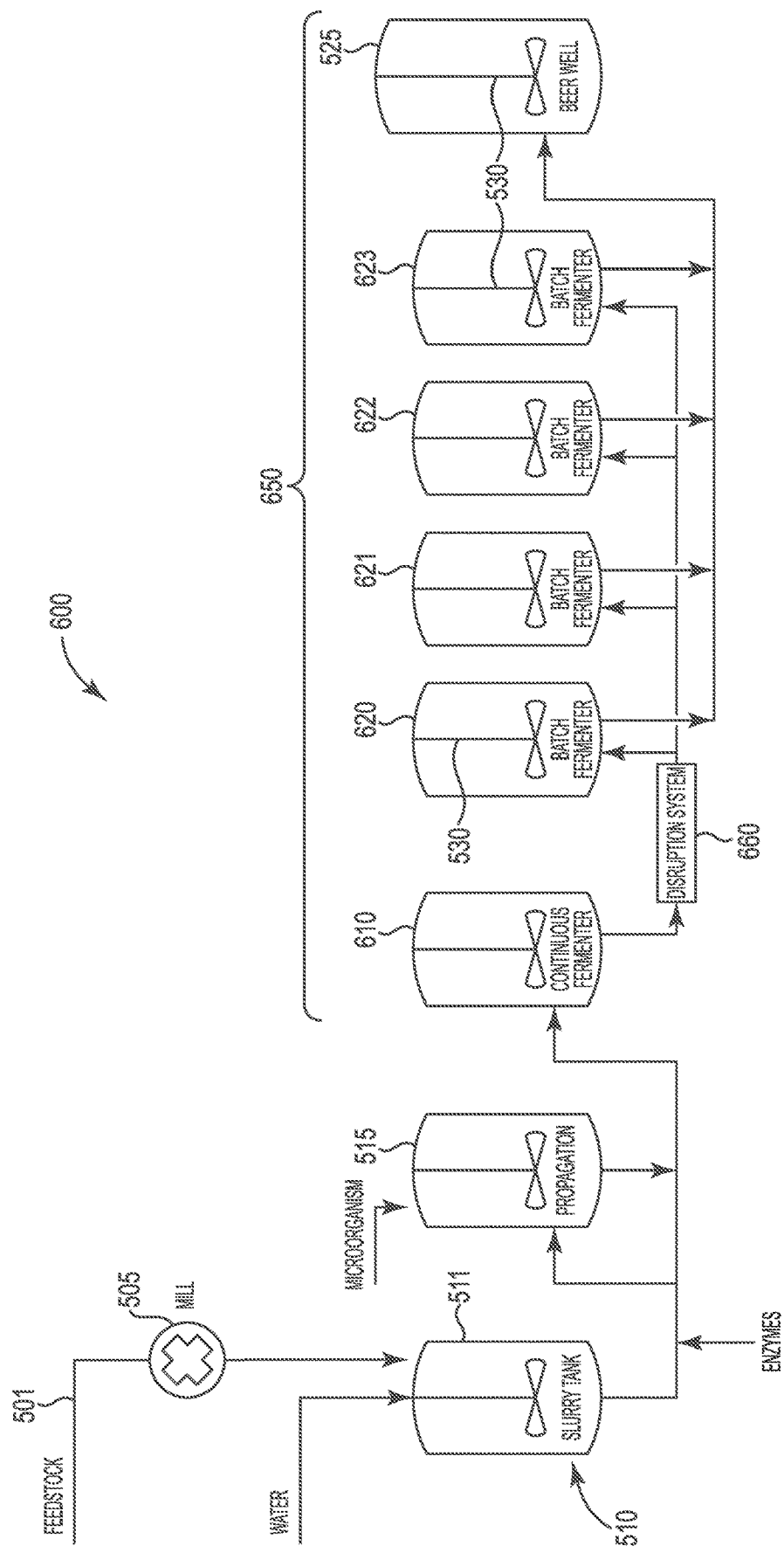
FIG. 6 shows a fermentation process flow diagram of another embodiment according to the present disclosure.
Figure 7:
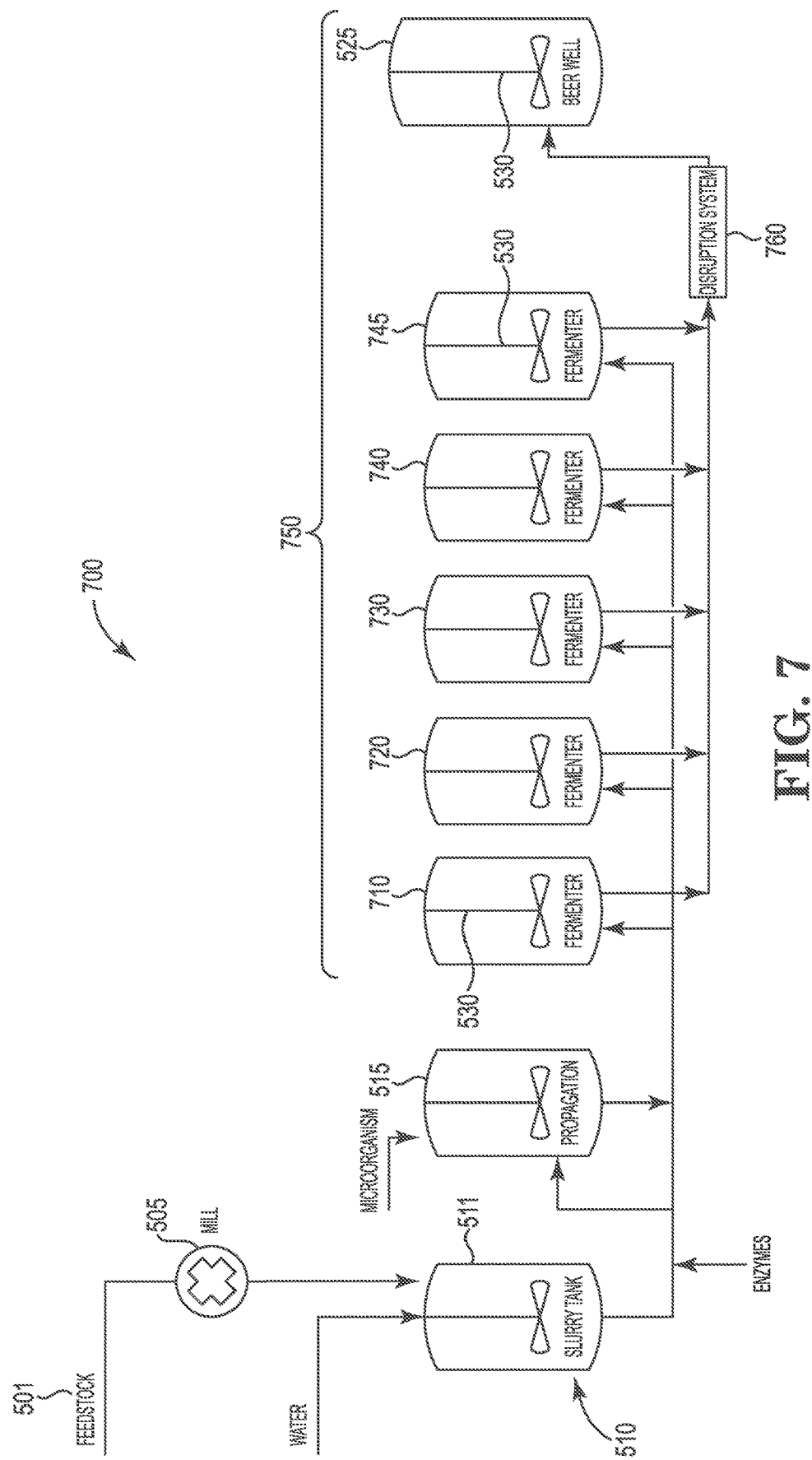
FIG. 7 shows a fermentation process flow diagram of another embodiment according to the present disclosure.
Figure 8:
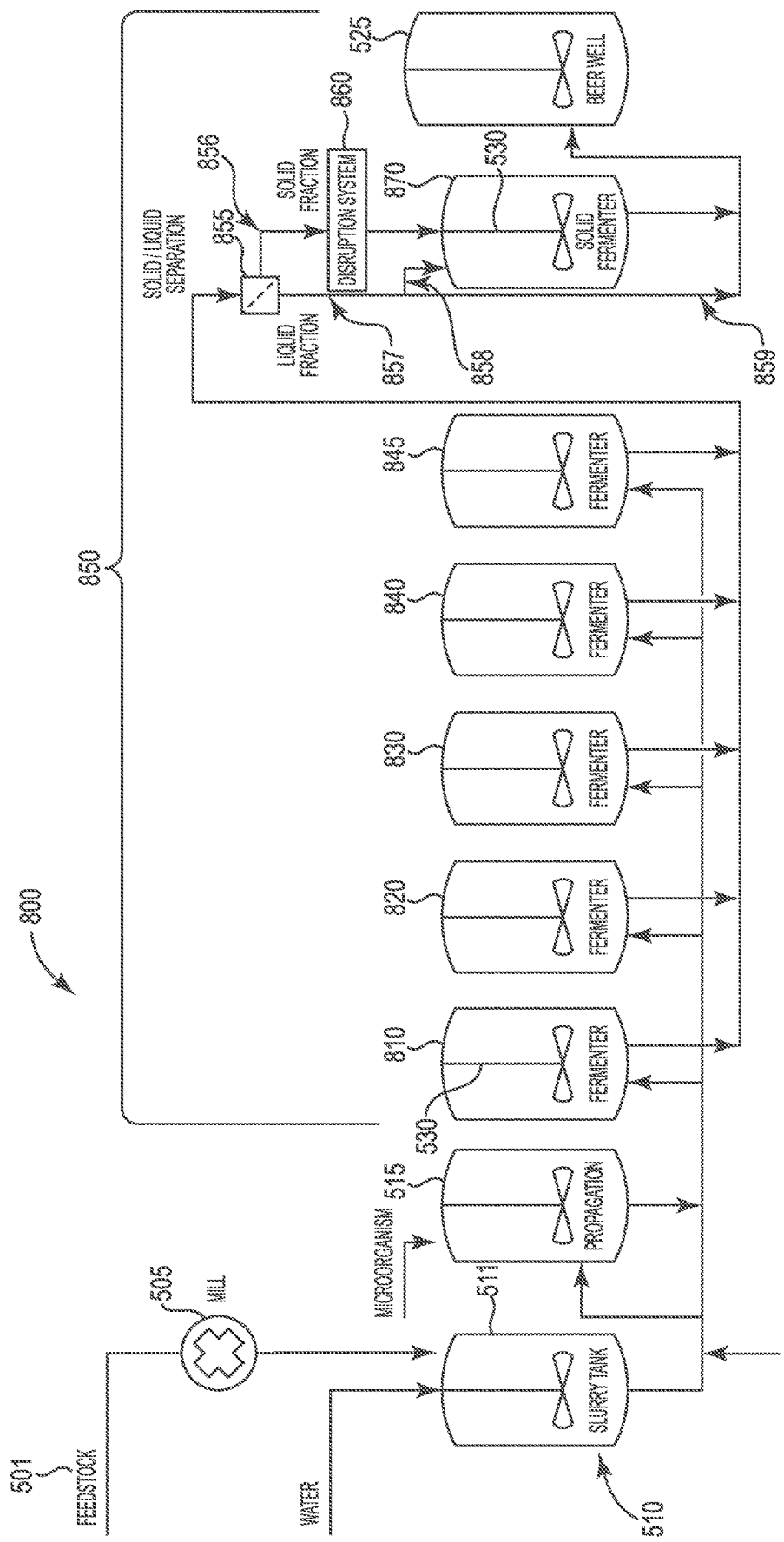
FIG. 8 shows a fermentation process flow diagram of another embodiment according to the present disclosure.

Additional non-limiting examples of disrupting biomass solids after the biomass solids have been exposed to fermentation are illustrated in FIGS. 6-8, which are described below. It is noted that each of the configurations incorporating disruption systems 560, 660, 760 and 860 can be used alone, as shown, or one or more configurations could be combined together if desired.

Like FIG. 5, FIG. 6 shows an embodiment of the present disclosure in the context of forming ethanol from corn grain. The same reference characters among FIGS. 5 and 6 illustrate the same features and their description is not repeated here. FIG. 6 illustrates a fermentation system 650 that incorporates a disruption system 660 that permits an entire fermentable composition to be exposed to the disruption system 660 in a single pass through the disruption system 660. Advantageously, recirculation as described above with respect to disruption system 560 and Table 1 can be avoided if desired. However, as mentioned above, the configurations incorporating disruption systems 560 and 660 could be combined together if desired.

In more detail, as shown in FIG. 6 a fermentable composition is exposed to conditions to convert at least a first portion of the saccharide component into alcohol via fermentation in fermenter 610, which is shown as operating in a continuous manner by continuously feeding and discharging fermentable composition from fermenter 610. This permits at least partial degradation of solid starch granules before being disrupted in a manner to cause at least further partial physical breakdown or degradation.

In addition, a fermentable composition in fermenter 610 can undergo fermentation for a time period as described herein above before being discharged downstream toward disruption system 660.

In some embodiments, the residence time of fermentable composition in fermenter 610 can be selected so that at least a portion of the fermenting microorganism is available for subsequent fermentation (e.g., in 620, 621, 622, or 623) and/or can tolerate disruption system 660 at the illustrated point in the overall fermentation system 650. For example, as discussed above, in the context of a yeast ethanologen, a target initial fermentation time in upstream fermentation (e.g., in fermenter 610), yeast density, ethanol titer, and/or yeast enzyme production can be used to determine the residence time of the fermentable composition before being exposed to disruption system 660. For example, in some embodiments, the fermentable composition may be fermented for a time that produces an ethanol concentration that is high enough to prevent bacterial growth/contamination from impacting subsequent yeast performance to an undue degree.

After being discharged from fermenter 610, the fermentable composition flows through a disruption system 660 and into at least one additional fermenter. As shown, after passing through disruption system 660, the fermentable composition is transferred into at least one of fermenters 620, 621, 622, or 623 so that saccharide component can be converted into alcohol via fermentation according to a batch process. Multiple batch fermenters can be filled in any desired manner. For example, the fermenters may be filled sequentially so that while fermenter 620 is being filled, each of the other fermenters 621, 622, and 623 are at a different stage of filling, fermenting, or emptying. Advantageously, adding exogenous fermenting microorganism to downstream fermenters (e.g., 620, 621, 622, or 623) can be avoided if desired.

As shown, the entire discharge of fermenter 610 passes through (flows through) the disruption system 660 once and into at least one of fermenters 620, 621, 622, or 623.

Optionally, if desired, equipment could be coupled to the discharge of disruption system 660 that separates solid particles based on size and recycles at least a portion of the fermentable composition discharged from disruption system 660 that includes solid particles larger than a target size back through disruption system 660 directly and/or upstream of system 660 such as via one or more of slurry tank 510 or fermenter 610.

Optionally, as mentioned above, a fermentable composition can be separated into a liquid fraction and a solid fraction using one or more solid-liquid separation apparatuses (not shown) prior to disruption system 660.

Another non-limiting example of disrupting biomass solids after the biomass solids have been exposed to fermentation is illustrated in FIG. 7. Like FIG. 5, FIG. 7 shows an embodiment of the present disclosure in the context of forming ethanol from corn grain. The same reference characters among FIGS. 5 and 7 illustrate the same features and their description is not repeated here. Like FIG. 6, FIG. 7 illustrates a fermentation system 750 that incorporates a disruption system 760 that permits an entire fermentable composition to be exposed to the disruption system 760 in a single pass through the disruption system 760. But, disruption system 760 is located after batch fermentation and, as shown, fermentation system 750 does not include a fermenter having continuous feed and discharge like fermenter 610 in FIG. 6. Advantageously, recirculation as described above with respect to disruption system 560 and Table 1 can be avoided if desired. However, as mentioned above, one or more of configurations incorporating disruption systems 560 and 660 could be combined with disruption system 760 if desired.

In more detail, as shown in FIG. 7 a fermentable composition is exposed to conditions to convert at least a first portion of the saccharide component into alcohol via fermentation in one of fermenters 710, 720, 730, 740 or 745, each of which is shown as operating in a batch manner. This permits at least partial degradation of solid starch granules before being disrupted in a manner to cause at least further partial physical breakdown or degradation of solid material including solid starch granules.

After being discharged from one of fermenters 710, 720, 730, 740 or 745, the entire discharge of fermentable composition flows through the disruption system 760 and into a vessel for additional fermentation. As shown, after passing through disruption system 760, the fermentable composition is transferred into beer well 525 so that saccharide component can be converted into alcohol via fermentation. In some embodiments, if desired, adding exogenous fermenting microorganism to beer well 525 can be avoided.

Batch fermenters 710, 720, 730, 740 or 745 can be discharged in any desired manner. For example, one fermenter can be discharged at a time or two or more fermenters can be discharged at the same time into a common header. Fermentable composition in beer well 525 can undergo fermentation while one or more of the other fermenters 710, 720, 730, 740 or 745 are being filled or undergoing fermentation. In some embodiments, although 710, 720, 730, 740 or 745 are operated according to a batch process, at least some of the batch operations are staggered from each other to permit the beer well 525 to be filled intermittently. Beer well 525 can have the capacity of more than one fermenter (e.g., two or more fermenters) to permit beer well 525 to be filled intermittently yet continuously discharge to distillation.

In some embodiments, a fermentable composition that is present in one or more of fermenters 710, 720, 730, 740 or 745 can undergo fermentation for a time period as described herein above before being discharged to disruption system 760. In some embodiments, the residence time of fermentable composition in one or more of fermenters 710, 720, 730, 740 or 745 can be selected so that at least a portion of the fermenting microorganism is available for subsequent fermentation (e.g., in beer well 525) and/or can tolerate disruption system 760 at the illustrated point in the overall fermentation system 750. For example, as discussed above, in the context of a yeast ethanologen, a target initial fermentation time in upstream fermentation (e.g., in fermenters 710, 720, 730, 740 or 745), yeast density, ethanol titer, and/or yeast enzyme production can be used to determine the residence time of the fermentable composition before being exposed to disruption system 760. For example, in some embodiments, the fermentable composition may be fermented for a time that produces an ethanol concentration that is high enough to prevent bacteria growth/contamination from impacting subsequent yeast performance to an undue degree.

As shown, the entire discharge (in any desired order) of each fermenter 710, 720, 730, 740 or 745 passes through (flows through) the disruption system 760 once and into beer well 525.

Optionally, as mentioned above, a fermentable composition can be separated into a liquid fraction and a solid fraction using one or more solid-liquid separation apparatuses (not shown) prior to disruption system 760.

Optionally, if desired, equipment could be coupled to the discharge of disruption system 760 that separates solid particles based on size and recycles at least a portion of the fermentable composition discharged from disruption system 760 that includes solid particles larger than a target size back through disruption system 760 directly and/or upstream of system 760 such as via at least one of slurry tank 510 and/or one or more fermenters 710, 720, 730, 740 or 745.

Another non-limiting example of disrupting biomass solids after the biomass solids have been exposed to fermentation is illustrated in FIG. 8. Like FIG. 5, FIG. 8 shows an embodiment of the present disclosure in the context of forming ethanol from corn grain. The same reference characters among FIGS. 5 and 8 illustrate the same features and their description is not repeated here. Like FIG. 7, FIG. 8 illustrates a fermentation system 850 that incorporates a disruption system 860 and that performs an initial batch fermentation on fermentable composition before performing a disruption process according to the present disclosure. Also, similar to FIGS. 6 and 7, FIG. 8 illustrates a fermentation system 850 that incorporates a disruption system 860 that processes an entire fermenter discharge stream through the disruption system 860 in a single pass. But, fermentation system 860 shows a solid-liquid separation apparatus 855 prior to disruption system 860 so that the solid fraction flows through the disruption system 860. As mentioned above, one or more of the configurations incorporating disruption systems 560, 660 or 760 could be combined with the configuration incorporating disruption system 860 if desired.

In more detail, as shown in FIG. 8 a fermentable composition is exposed to conditions to convert at least a first portion of the saccharide component into alcohol via fermentation in one of fermenters 810, 820, 830, 840 or 845, each of which is shown as operating in a batch manner. This permits at least partial degradation of solid starch granules before being disrupted in a manner to cause at least further partial physical breakdown or degradation.

In some embodiments, a fermentable composition in one or more of fermenters 810, 820, 830, 840 or 845 can undergo fermentation for a time period as described herein above before being discharged downstream toward disruption system 860. In some embodiments, the residence time of fermentable composition in one or more of fermenters 810, 820, 830, 840 or 845 can be selected so that at least a portion of the fermenting microorganism is available for subsequent fermentation (e.g., in fermenter 870) and/or can tolerate disruption system 860 at the illustrated point in the overall fermentation system 850. For example, as discussed above, in the context of a yeast ethanologen, a target initial fermentation time in upstream fermentation (e.g., in fermenters 810, 820, 830, 840 or 845), yeast density, ethanol titer, and/or yeast enzyme production can be used to determine the residence time of the fermentable composition before being exposed to disruption system 860. For example, in some embodiments, the fermentable composition may be fermented for a time that produces an ethanol concentration that is high enough to prevent bacterial growth/contamination from impacting subsequent yeast performance to an undue degree.

Batch fermenters 810, 820, 830, 840 and 845 can be discharged in any desired manner. For example, one fermenter can be discharged at a time or two or more fermenters can be discharged at the same time into a common header.

After being discharged from one of fermenters 810, 820, 830, 840 or 845, the fermentable composition flows through one or more solid-liquid separation apparatuses such as solid-liquid separation apparatus 855 to separate the fermentable composition into a liquid fraction 857 and a solid fraction 856. The solid fraction includes saccharide component and flows through disruption system 860 to disrupt the solids and expose additional polysaccharide that can be hydrolyzed into monosaccharide for fermentation. As shown in FIG. 8, disruption system 860 is a milling system that can reduce the particle size of the biomass solids. In some embodiments, separating the solids prior to disruption system 860 can reduce the required capacity, and therefore the size, of disruption system 860, which can provide capital savings. Also, in some embodiments, separating the solids prior to disruption system 860 and fermenter 870 can reduce the overall fermentation time in fermenter 870 as compared to if the entire liquid fraction 857 in fermentable composition prior to solid-liquid separation apparatus 855 was instead transferred to fermenter 870.

After being exposed to disruption system 860, the solids fraction flows into a vessel for additional fermentation. As shown in FIG. 8, after passing through disruption system 860, the solids fraction is transferred into a fermenter 870 so that saccharide component can be converted into alcohol via fermentation according to a batch or continuous process. The solid fraction 856 can be combined with a liquid in fermenter 870 to help provide a less viscous (more flowable) slurry that can be pumped and mixed (e.g., using stirring mechanism 530). A wide variety of aqueous liquids (process streams and/or fresh water) can be combined with solid fraction 856. As shown in FIG. 8, at least a portion 858 of the liquid fraction 857 discharged from solid-liquid separation apparatus 855 is combined with the solid fraction in fermenter 870. The liquid fraction can include active yeast cells that can convert saccharide component in fermenter 870 into biochemical. In some embodiments, if desired, adding exogenous fermenting microorganism to fermenter 870 can be avoided. Fermentation can be performed in fermenter 870 while one or more of the other fermenters 810, 820, 830, 840 or 845 are being filled or undergoing fermentation.

As shown, the entire discharge from fermenter 870 and liquid fraction 859 from solid-liquid separation apparatus 855 flows into beer well 525.

Optionally, if desired, equipment could be coupled to the discharge of disruption system 860 that separates solid particles based on size and recycles at least a portion of the solid fraction discharged from disruption system 860 that includes solid particles larger than a target size back through disruption system 860 directly and/or via at least one of slurry tank 510 and/or upstream of system 860 such as one or more fermenters 810, 820, 830, 840 or 845.

After fermentation, biochemical and/or one or more by-products and/or one or more co-products can be separated and recovered according to any desired technique. For example, when the biochemical is ethanol, ethanol can be distilled from fermentation beer to form whole stillage. Because relatively more polysaccharide can be accessed and hydrolyzed into monosaccharide such as glucose, a relatively higher conversion of polysaccharide to ethanol can be achieved using a disruption process according to the present disclosure as compared to not using a disruption process according to the present disclosure.

Likewise, it is believed that relatively more one or more co-products can be separated and recovered using a disruption process according to the present disclosure as compared to not using a disruption process according to the present disclosure.

For example, when the biomass includes whole corn, corn oil can be separated and recovered form one or more process streams downstream from biochemical recovery (e.g., one or more of whole stillage, wet cake, thin stillage, and concentrated thin stillage). As discussed below, it is believed that Example 2 supports the position that relatively higher separation and recovery of corn oil can be achieved using a disruption process according to the present disclosure as compared to not using a disruption process according to the present disclosure. Corn oil can be recovered by any desired technique. Nonlimiting examples of separating corn oil from process streams in a biorefinery include U.S. Pat. Nos. 9,061,987 (Bootsma), 8,702,819 (Bootsma), 9,695,449 (Bootsma), 8,008,516 (Cantrell et al.) and U.S. Patent Publication 2019/0376002 (Urban et al.), wherein the entirety of each of said patent document is incorporated herein by reference.

Example 1

Fermentation broth from a commercial dry mill ethanol facility was processed in a single pass through a disc mill after the fermentation batch had fermented for 21.5 hours. Without adding any additional exogenous yeast, the milled sample and a control non-milled sample were both fermented in duplicate at 88F for an additional 72 hours in a lab environment. At the end of the lab fermentation the non-milled sample was 19.8% v/v ethanol and the milled sample was 20.4% v/v ethanol.

Example 2

Figure 9:
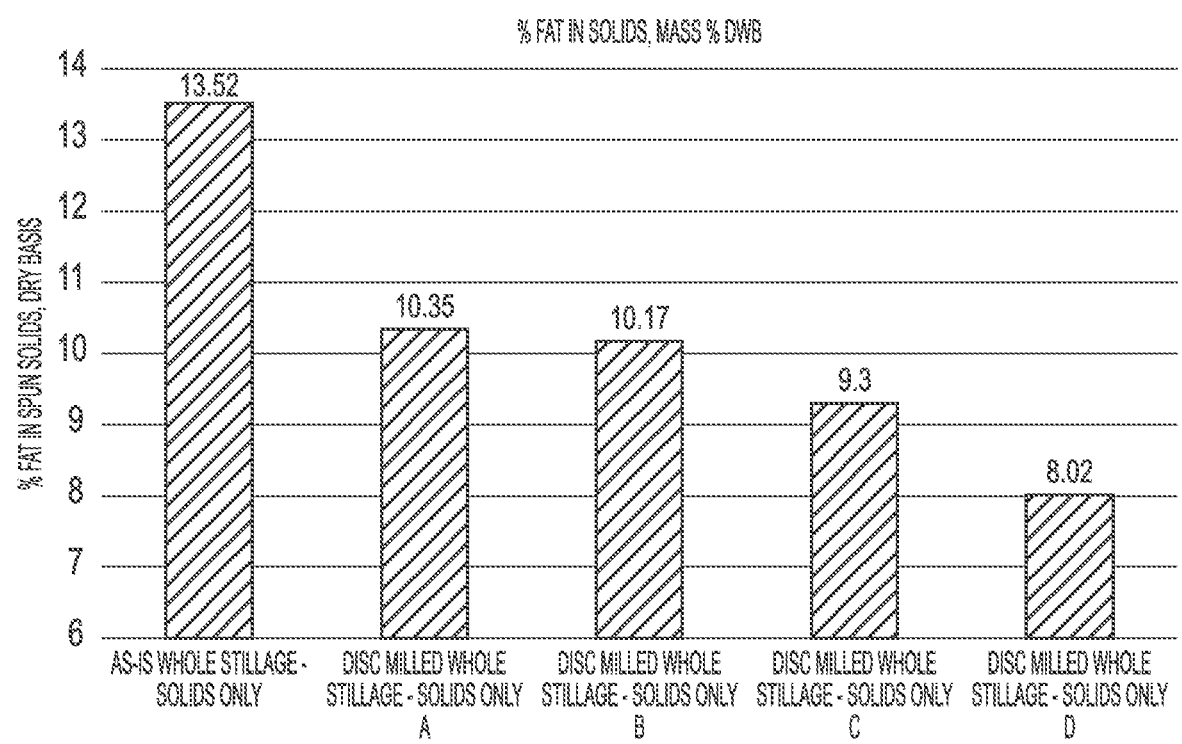
FIG. 9 is a graph showing percent fat in solids for samples from Example 2.

Example 2 generated data (illustrated in FIG. 9) indicating that corn oil yield from whole stillage (or composition derived therefrom such as wet cake and/or thin stillage and/or syrup) can be increased by mechanical milling during fermentation according to the present disclosure. For this trial, whole stillage was recirculated from a bucket placed under the discharge of a disc mill and back up to the entry hopper of the disc mill. The whole stillage passed through the disc mill and fell back into the bucket. In this way, whole stillage was recirculated many times through the disc mill. Samples were recovered for as-is whole stillage and as milling progressed from times "A" to "B" to "C" to "D". Time "B" was one hour after "A", time "C" was one hour after time "B", and time "D" was thirty minutes after time "C." The milled samples were centrifuged in the lab to give a centrifuge tube with a solid pellet on the bottom (a pellet of packed solids) and a clarified liquid on top of the pellet. The liquid was poured off and the fat in the pellet was measured. A lower amount of fat in the pellet indicates that more oil/fat was released from the pellet and into the liquid. Since corn oil is recovered from the liquid portion (e.g., corn oil can be recovered from thin stillage and/or concentrated thin stillage/syrup), these results suggest that milling can be used to transfer fat from the solids to the liquid fraction for improved corn oil recovery.

What is claimed is:

1. A method of fermenting, wherein the method comprises:
    a) providing a fermentable composition, wherein the fermentable composition comprises:
        i) biomass, wherein the biomass comprises a solid component and a saccharide component; and
        ii) a microorganism that can convert monosaccharide into a biochemical, wherein the microorganism comprises yeast,
    b) exposing the fermentable composition to conditions to convert at least a first portion of the saccharide component into a biochemical via fermentation;
    c) after performing step (b) for at least 12 hours,
        i) exposing at least a portion of the fermentable composition to a disruption process to disrupt at least a portion of insoluble solid component; and
        ii) during and/or after (c)(i), converting at least a second portion of the saccharide component into biochemical via fermentation.

2. The method of claim 1, wherein exposing the fermentable composition to conditions to convert at least a first portion of the saccharide component into biochemical via fermentation occurs in a first fermenter, and wherein exposing at least a portion of the fermentable composition to a disruption process comprises:
    a) discharging fermentable composition from the first fermenter; and
    b) passing the fermentable composition through a disruption system and into a second fermenter,
wherein converting at least a second portion of the saccharide component into biochemical via fermentation occurs in the second fermenter.

3. The method of claim 2, wherein the entire contents of the first fermenter pass through the disruption system once and into the second fermenter, wherein the first fermenter is separate from the second fermenter.

4. The method of claim 2, wherein the first fermenter continuously receives and discharges fermentable composition, and wherein the second fermenter operates according to a batch process.

5. The method of claim 4, further comprising:
    a) a third fermenter;
    b) discharging additional fermentable composition from the first fermenter; and
    c) passing the fermentable composition through the disruption system and into the third fermenter.

6. The method of claim 2, wherein the first fermenter and the second fermenter each operate according to a batch process.

7. The method of claim 3, further comprising:
   a) a fermentation system comprising a plurality of fermenters, wherein the plurality of fermenters comprises the first fermenter, the second fermenter, and at least one additional fermenter;
   b) while exposing the fermentable composition to conditions to convert at least a first portion of the saccharide component into alcohol via fermentation occurs in the first fermenter, filling the at least one additional fermenter with fermentable composition;
   c) after the entire contents of the first fermenter pass through the disruption process once and into the second fermenter, passing the fermentable composition from the at least one additional fermenter through the disruption system and into the first fermenter.

8. The method of claim 1, wherein exposing the fermentable composition to conditions to convert at least a first portion of the saccharide component into alcohol via fermentation occurs in a first fermenter, and wherein exposing at least a portion of the fermentable composition to a disruption process comprises:
   a) discharging the fermentable composition from the first fermenter; and
   b) passing the fermentable composition through a disruption system; and
   c) recycling at least a portion of the fermentable composition from the disruption system to the first fermenter, wherein converting at least a second portion of the saccharide component into alcohol via fermentation occurs in the first fermenter.

9. The method of claim 8, wherein, during a total time period of the recycling, a total volume of fermentable composition discharged from the first fermenter and through the disruption system divided by the first fermenter volume is 10 or less.

10. The method of claim 1, wherein, prior to exposing at least a portion of the fermentable composition to a disruption process, separating the fermentable composition into a liquid fraction and a solid fraction, wherein the solid fraction comprises the second portion of the saccharide component, wherein exposing at least a portion of the fermentable composition to a disruption process comprises exposing at least a portion of the solid fraction to the disruption process.

11. The method of claim 10, wherein, during a total time period of the recycling, a total volume of solid fraction through the disruption system divided by the first fermenter volume is 5 or less.

12. The method of claim 10, wherein, after exposing at least a portion of the solid fraction to the disruption process and prior to converting the at least a second portion of the saccharide component into alcohol via fermentation, combining the solid fraction with a liquid.

13. The method of claim 12, where the liquid comprises at least a portion of the liquid fraction.

14. The method of claim 10, wherein the fermentable composition is separated into the liquid fraction and the solid fraction via one or more solid-liquid separation apparatuses, wherein the one or more solid-liquid separation apparatuses are chosen from a centrifuge, a gravity screen, a hydroclone, a filter press, a rotary paddle screen, a screw press, a gravity settler, a membrane filter, a cartridge filter, and combinations thereof.

15. The method of claim 1, wherein exposing the fermentable composition to conditions to convert at least a first portion of the saccharide component into biochemical via fermentation permits solid saccharide component to at least partially break down via hydrolysis prior to exposing the biomass to the disruption process.

16. The method of claim 1, wherein no additional yeast is exogenously added to the fermentable composition after the exposing at least a portion of the fermentable composition to a disruption process.

17. The method of claim 1, wherein the disruption process comprises subjecting the at least a portion of the fermentable composition to one or more disc mills, roller mills, a colloid mills, disk refiners, homogenizers, rotary impact mills, jet mills, ball mills, tube mills, pebble mills, rod mills, impact mills, cone mills, centrifugal mills, high sheer pumps, high sheer rotor stator mixers, screw presses, French presses, and combinations thereof.

18. The method of claim 1, wherein providing the fermentable composition comprises combining biomass, one or more enzymes that can hydrolyze a polysaccharide and/or an oligosaccharide into monosaccharide, yeast, and a water composition to form the fermentable composition.

19. The method of claim 1, wherein the biomass comprises whole ground corn formed via a dry-grind process, wherein the biochemical comprises ethanol, and wherein exposing the fermentable composition to conditions to convert at least a first portion of the saccharide component into a biochemical via fermentation occurs via simultaneous saccharification and fermentation.

20. The method of claim 1, wherein exposing the fermentable composition to conditions to convert at least a first portion of the saccharide component into a biochemical via fermentation comprises:
   a) hydrolyzing at least a first portion of the saccharide component under a first set of conditions in a hydrolysis system to form monosaccharide; and
   b) after "a", fermenting monosaccharide under a second set of conditions in a fermentation system, wherein the hydrolysis system is different than the fermentation system, and wherein the first set of conditions is different than the second set of conditions.

21. The method of claim 20, wherein the biomass comprises whole ground corn formed via a dry-grind process, wherein the biochemical comprises ethanol, and further comprising:
   a) distilling ethanol from fermentation beer to form whole stillage; and
   b) separating corn oil from one or more of whole stillage, wet cake, thin stillage, and concentrated thin stillage.

22. The method of claim 21, further comprising, prior to "b," exposing at least a portion of the whole stillage to a disruption process to disrupt at least a portion of insoluble solid component.

23. A method of fermenting, wherein the method comprises:
   a) providing a fermentable composition, wherein the fermentable composition comprises:
      i) biomass, wherein the biomass comprises a solid component and a saccharide component; and
      ii) yeast,
   b) exposing the fermentable composition to conditions to convert at least a first portion of the saccharide component into alcohol via fermentation;
   c) after forming an alcohol titer in step (b) of at least 1% v/v based on the fermentable composition,
      i) exposing at least a portion of the fermentable composition to a disruption process to disrupt at least a portion of insoluble solid component; and ii) during and/or after (c)(i), converting at least a second portion of the saccharide component into alcohol via fermentation.

24. A method of fermenting, wherein the method comprises:
   a) providing a fermentable composition, wherein the fermentable composition comprises:
      i) biomass, wherein the biomass comprises a solid component and a saccharide component; and
      ii) yeast;
   b) exposing the fermentable composition to conditions to convert at least a first portion of the saccharide component into alcohol via fermentation, and reproduce yeast;
   c) after the yeast is at a density of at least $1\times10^6$ yeast cells per milliliter of fermentable composition in step (b),
      i) exposing at least a portion of the fermentable composition to a disruption process to disrupt at least a portion of insoluble solid component; and
      ii) during and/or after (c)(i), converting at least a second portion of the saccharide component into alcohol via fermentation.

* * * * *